United States Patent [19]  
Lacefield

[11] 3,989,831  
[45] Nov. 2, 1976

[54] TOPICALLY-ACTIVE ANTI-INFLAMMATORY 3-CHLORO-5,6-DIARYL-1,2,4-TRIAZINES

[75] Inventor: William B. Lacefield, Indianapolis, Ind.

[73] Assignee: Eli Lilly and Company, Indianapolis, Ind.

[22] Filed: Mar. 10, 1976

[21] Appl. No.: 665,591

Related U.S. Application Data

[63] Continuation-in-part of Ser. No. 438,156, Jan. 31, 1974, Pat. No. 3,948,894.

[52] U.S. Cl. ............................ 424/249; 260/248 AS
[51] Int. Cl.$^2$ ................. C07D 253/06; A61K 31/53
[58] Field of Search ................ 260/248 AS; 424/249

[56] References Cited
OTHER PUBLICATIONS

Polonovski et al., Chemical Abstracts, vol. 46, 514(b) 1952.

*Primary Examiner*—John M. Ford
*Attorney, Agent, or Firm*—William E. Maycock; Everet F. Smith

[57] ABSTRACT

3-Chloro-5,6-diaryl-1,2,4-triazines, topically active anti-inflammatory agents, having the formula

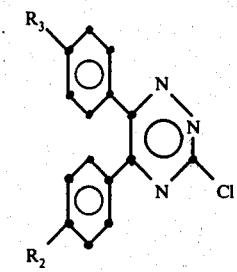

wherein $R_2$ and $R_3$ independently are halo, $C_1$–$C_3$ alkyl, $C_1$–$C_3$ alkoxy, or di($C_1$–$C_3$ alkyl)amino; and the pharmaceutically-acceptable acid addition salts of basic members thereof.

19 Claims, No Drawings

TOPICALLY-ACTIVE ANTI-INFLAMMATORY 3-CHLORO-5,6-DIARYL-1,2,4-TRIAZINES

CROSS-REFERENCE TO RELATED APPLICATION

This application is a continuation-in-part of copending application Ser. No. 438,156, filed Jan. 31, 1974, now U.S. Pat. No. 3,948,894.

BACKGROUND OF THE INVENTION

This invention relates to topically-active anti-inflammatory 3-chloro-5,6-diaryl-1,2,4-triazines, to a method of treating inflammation, and to a composition suitable for treating inflammation.

Inflammation is an essentially protective and normal response to injury, although the etiology and pathogenesis of many inflammatory conditions remain obscure. In general, anti-inflammatory agents are employed primarily to relieve the symptoms of inflammation. In such symptomatic therapy, topically-applied anti-inflammatory agents present special problems. Inflammatory conditions calling for the topical application of an anti-inflammatory agent are almost exclusively treated with steroids. Topically applied steroids, however, may carry considerable systemic toxicity. Thus, the need continues for safer, better tolerated topically active anti-inflammatory agents.

3-Chloro-1,2,4-triazines are disclosed generically as intermediates in Swiss Pat. No. 480,795. Such triazines are substituted in the 5- and/or 6-position with alkyl, cycloalkyl, or aryl moieties optionally substituted by one of the following groups: halo, alkyl, alkoxy, nitro, alkylamino, dialkylamino, acylamino, and alkoxycarbonyl. The compounds have no disclosed utility except as intermediates in the preparation of 3-amino-1,2,4-triazine-N-oxides which are useful as plant growth-control agents and weed killers. Most of the specific examples of the 3-amino compounds are 3-amino-5,6-diphenyl-1,2,4-triazine-N-oxides, although in two instances the 5- and 6-substituents are p-methylphenyl groups.

SUMMARY OF THE INVENTION

In accordance with the present invention, 3-chloro-5,6-diaryl-1,2,4-triazines are provided having the formula,

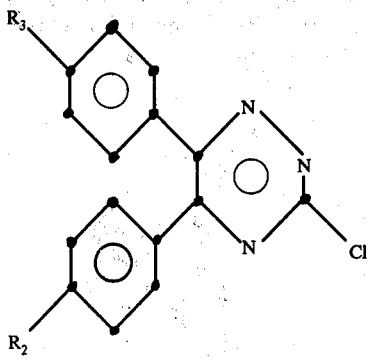

wherein $R_2$ and $R_3$ independently are halo, $C_1$–$C_3$ alkoxy, or di($C_1$–$C_3$ alkyl)amino;
and the pharmaceutically acceptable acid addition salts of basic members thereof.

Also in accordance with the present invention, a method of treating inflammation in a warm-blooded mammal is provided which comprises topically administering to such mammal an effective amount of a compound of the formula, wherein $R_2$ and $R_3$ independently are halo, $C_1$–$C_3$ alkyl, $C_1$–$C_3$ alkoxy, or di($C_1$–$C_3$ alkyl)amino; and the pharmaceutically acceptable acid addition salts of basic members thereof.

The present invention also provides a composition suitable for topically treating inflammation in a warm-blooded mammal which comprises a pharmaceutically acceptable carrier and an effective amount of a compound as defined hereinabove for use in the method of the present invention.

As used herein, "an effective amount" means an amount sufficient to at least in part ameliorate the inflammatory condition under treatment. The relief afforded thereby can be observed as a reduction in the intensity of the inflammation, a reduction in the time period during which the inflammatory condition persists, or both, and in instances where pretreatment is possible, a delay in the appearance of the inflammatory condition also can be observed.

The compounds of the present invention and the compounds employed in the method and composition of the present invention are useful as topically active anti-inflammatory agents in warm-blooded mammals, such as guinea pigs, mice, rats, dogs, monkeys, humans, and the like.

DETAILED DESCRIPTION OF THE INVENTION

The term "$C_1$–$C_3$ alkoxy" includes methoxy, ethoxy, propoxy, and isopropoxy. The term "$C_1$–$C_3$ alkyl" includes methyl, ethyl, propyl, and isopropyl. The term "halo" includes fluoro, chloro, bromo, and iodo.

Illustrative of the triazine compounds which are useful in the present invention are the following:
3-chloro-5,6-bis(4-fluorophenyl)-1,2,4-triazine,
3-chloro-5,6-bis(4-chlorophenyl)-1,2,4-triazine,
5,6-bis(4-bromophenyl)-3-chloro-1,2,4-triazine,
3-chloro-5,6-bis(4-iodophenyl-1,2,4-triazine,
3-chloro-5,6-bis(4-methylphenyl)-1,2,4-triazine,
3-chloro-5,6-bis(4-ethylphenyl)-1,2,4-triazine,
3-chloro-5,6-bis(4-propylphenyl)-1,2,4-triazine,
3-chloro-5,6-bis(4-isopropylphenyl)-1,2,4-triazine,
3-chloro-5,6-bis(4-methoxyphenyl)-1,2,4-triazine,
3-chloro-5,6-bis(4-ethoxyphenyl)-1,2,4-triazine,
3-chloro-5,6-bis(4-propoxyphenyl)-1,2,4-triazine,
3-chloro-5,6-bis(4-isopropoxyphenyl)-1,2,4-triazine,
3-chloro-5,6-bis(4-dimethylaminophenyl)-1,2,4-triazine,
3-chloro-5,6-bis(4-diethylaminophenyl)-1,2,4-triazine,
3-chloro-5,6-bis(4-dipropylaminophenyl)-1,2,4-triazine,
3-chloro-5,6-bis(4-diisopropylaminophenyl)-1,2,4-triazine, 6-(4-bromophenyl)-3-chloro-5-(4-fluorophenyl)-1,2,4-triazine,
3-chloro-5-(4-chlorophenyl)-6-(4-propylphenyl)-1,2,4-triazine,
5-(4-bromophenyl)-3-chloro-6-(4-isopropoxyphenyl)-1,2,4-triazine,
3-chloro-5-(4-dipropylaminophenyl)-6-(4-fluorophenyl)-1,2,4-triazine,
3-chloro-6-(4-ethylphenyl)-5-(4-methylphenyl)-1,2,4-triazine,
3-chloro-5-(4-isopropoxyphenyl)-6-(4-methylphenyl)-1,2,4-triazine,
3-chloro-6-(4-dimethylaminophenyl)-5-(4-isopropylphenyl)-1,2,4-triazine,
3-chloro-5-(4-ethoxyphenyl)-6-(4-methoxyphenyl)-1,2,4-triazine,
3-chloro-6-(4-diisopropylaminophenyl)-5-(4-methoxyphenyl)-1,2,4-triazine,
3-chloro-6-(4-diethylaminophenyl)-5-(4-dimethylaminophenyl)-1,2,4-triazine, and the like, and the pharmaceutically-acceptable acid addition salts of the basic triazines.

The preferred triazines provided by the present invention are those wherein $R_2$ and $R_3$ in the above-defined formula are $C_1$–$C_3$ alkoxy. More preferably, $R_2$ and $R_3$ will be the same, and most preferably are methoxy.

Examples of such preferred, more preferred, and most preferred triazines are included in the above list of illustrative triazines.

The compounds of the present invention and the compounds employed in the method and composition of the present invention are prepared by a variety of methods known to those having ordinary skill in the art. Starting materials and intermediates also are prepared by known methods. The preparation of 5,6-diaryl-1,2,4-triazines is described generally by J. G. Erickson in "The 1,2,3- and 1,2,4-Triazines, Tetrazines and Pentazines," The Chemistry of Heterocyclic Compounds, Vol. 10, Interscience Publishers, Inc., New York, N.Y., 1956, Chapter II, pp. 44–84.

3-Chloro-5,6-diaryl-1,2,4-triazines are readily obtained by treating the appropriate 3-hydroxytriazine with a suitable halogenating reagent, such as phosphorus pentachloride and phosphorus oxychloride, with phosphorus oxychloride being preferred. See, for example, M. Polonovski, et al., Compt. rend., 235, 1310 (1953) [Chem. Abstr., 47: 11209e (1953)]; M. Polonovski, et al., Bull. soc. chim. France, 1955, 240 [Chem. Abstr., 50: 1840f (1956)]; and P. V. Laakso, et al., Tetrahedron, 1, 103 (1957) [Chem. Abstr., 51: 13875i (1957)]. 3-Hydroxy-5,6-diaryl-1,2,4-triazines in turn can be prepared by condensing an appropriate benzil with semicarbazide.

The required benzils are prepared by the oxidation of the corresponding benzoins with copper sulfate in pyridine; see H. T. Clarke and E. E. Driger, Org. Synthesis, Coll. Vol. I, 87 (1941). The benzoins are prepared by the condensation of aromatic aldehydes with cyanide ion; see W. S. Ide and J. S. Buck, Org. Reactions, 4, 269 (1948).

Another approach to the compounds useful in the present invention involves the use of benzils having substituents which can be displaced to give the desired $R_2$ or $R_3$ substituent. For example, the halogen on the phenyl ring at the 5-position in 3-chloro-5-(4-halophenyl)-6-aryl-1,2,4-triazines can be displaced with an alcohol or a dialkylamine to give the corresponding 5-(4-alkoxyphenyl)- or 5-(4-dialkylaminophenyl)-compound, respectively.

The use of two different aromatic aldehydes in the benzoin synthesis leads to unsymmetrical benzils. That is, in a benzil of the formula,

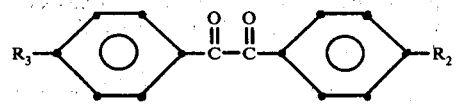

wherein $R_2$ and $R_3$ are as described hereinbefore, $R_2$ and $R_3$ are different. The use of an unsymmetrical benzil may result in the preparation of a mixture of triazine isomers. For example, the condensation of 4-dimethylamino-4'-methoxybenzil with semicarbazide gives a mixture of 5-(4-dimethylaminophenyl)-3-hydroxy-6-(4-methoxyphenyl-1,2,4-triazine and 6-(4-dimethylaminophenyl)-3-hydroxy-5-(4-methoxyphenyl)-1,2,4-triazine.

It will be recognized by those skilled in the art that mixtures of triazine isomers are separable by known methods, such as fractional crystallization and chromatography. The isomer separation may be effected upon intermediate mixtures or delayed until the final product stage.

Certain of the 3-chloro-5,6-diaryl-1,2,4-triazines described herein are sufficiently basic to form acid addition salts, especially when the triazine contains one or more alkylamino groups on the phenyl rings. "Pharmaceutically acceptable" acid addition salts are well known to those skilled in the art and in general are formed by reacting in a mutual solvent a stoichiometric amount of a suitable acid with a basic triazine. Such salts should not be substantially more toxic to warm-blooded animals than the triazines. While the choice of a salt-forming acid is not critical, in some instances a particular acid may result in a salt having special advantages, such as ready solubility, ease of crystallization, and the like. Representative and suitable acids include, among others, the following: hydrochloric, hydrobromic, hydriodic, sulfuric, nitric, phosphoric, methanesulfonic, p-toluenesulfonic, and the like.

As stated hereinbefore, the present invention also provides a method of treating inflammation in a warm-blooded mammal which comprises topically administering to such mammal an effective amount of a compound of the formula,

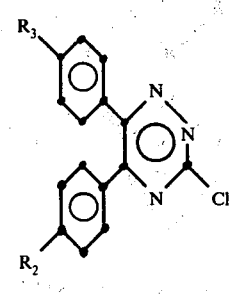

wherein $R_2$ and $R_3$ independently are halo, $C_1$–$C_3$ alkyl, $C_1$–$C_3$ alkoxy, or di($C_1$–$C_3$ alkyl)amino; and the pharmaceutically acceptable acid addition salts of basic members thereof.

The present invention also provides a composition suitable for topically treating inflammation in a warm-blooded mammal which comprises a pharmaceutically acceptable carrier and an effective amount of a compound as defined hereinabove for use in the method of the present invention.

The preferred compounds for use in the method and composition of the present invention are those wherein $R_2$ and $R_3$ in the above-defined formula are $C_1$–$C_3$ alkoxy. More preferably, $R_2$ and $R_3$ will be the same, and most preferably are methoxy. Illustrative of the compounds which can be employed in the method and composition of the present invention, as well as such preferred, more preferred, and most preferred compounds, are the triazines illustrative of the compounds useful in the present invention, described hereinabove.

A modification of the method of Winder was used to measure the anti-inflammatory activities of the compounds of the present invention and the compounds employed in the method and composition of the present invention; see C. V. Winder, et al., Arch. Int. Pharmacodyn., 116, 261 (1958). Albino guinea pigs of either sex, weighing 225–300 grams, were shaved on the back and chemically depilated (Nair Lotion Hair Remover, Carter Products, N.Y., N.Y.) 18–20 hours before exposure to ultraviolet light. The animals, in groups of four and bearing identifying ear tags, were treated by applying to an area of skin of about 12 cm.$^2$ a solution of test compound dissolved in 0.1 cc. of ethanol. The control treatment consisted of administering only the drug vehicle, ethanol, to a group of four animals. Groups of four animals each were given different treatment levels of test compounds to obtain dose responses. Random order and blind administration of the test compounds were employed; drug identification was not made until after all animals were graded. Immediately prior to drug application, the animals were exposed in groups of four to a high-intensity ultraviolet light for a measured period of time (usually 4–7 seconds). The ultraviolet light source, a Hanovia Lamp (Kroymayer-Model 10), was placed in contact with the skin of the animal's back. A gummed notebook paper reinforcement was affixed to the lamp lens to provide an unexposed area of contrast for grading the erythema. Beginning one hour after exposure and thereafter at half-hour intervals for another 1½ hours, the degree of resulting erythema was graded by an arbitrary scoring system based upon the degree of contrast and redness formed. Anti-inflammatory agents delay the development of the erythema and usually have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Erythema Scoring System | |
|---|---|
| Score | Appearance of Exposed Area |
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs were compared to the control treatment, and the percent inhibition was calculated as follows:

$$100 \times \frac{\text{Control Score} - \text{Treatment Score}}{\text{Control Score}} = \text{Percent Inhibition}$$

A dose-response graph is obtained by plotting dose versus the average percent inhibition of each treatment group of four guinea pigs. The dose ($ED_{50}$) in micrograms per 12 cm.$^2$ (mcg./12 cm.$^2$) which produces a 50 percent inhibition of the erythemic response for the particular compound tested is obtained by extrapolation. In general, the 3-chlorotriazines useful in the present invention result in at least 20 percent inhibition at dose levels below about $10^3$ mcg./12 cm.$^2$ For example, 3-chloro-5,6-bis(4-methoxyphenyl)-1,2,4-triazine gives 46 percent inhibition at $10^2$ mcg./12 cm.$^2$ The toxicities of representative compounds of the present invention and compounds employed in the method and composition of the present invention, determined as the dose ($LD_{50}$) in milligrams per kilogram (mg./kg.) of animal body weight which is lethal to 50 percent of mice treated orally, typically are greater than about 1000 mg./kg., and in some cases are greater than about 1500 mg./kg.

The method and composition of the present invention can be used in the treatment of a variety of inflammatory conditions which are susceptible to treatment with topically active anti-inflammatory agents. Such inflammatory conditions include, among others, atropic dermatitis, contact dermatitis, nummular eczema, lichen simplex, psoriasis, chronic dermatoses, and ultraviolet-induced erythema.

The method and composition of the present invention are especially useful in the treatment of inflammation induced by intraviolet radiation, the most common example of such inflammation being sunburn.

In the practice of the method of this invention, one (or more) of the anti-inflammatory triazines is topically administered to a warm-blooded mammal in an effective amount, i.e., an amount effective for the topical treatment of inflammation. In general, such effective amount will be at least about 1 mcg. of triazine per 12 cm.$^2$ of skin surface area (1 mcg./12 cm.$^2$). Because of the relatively low order of toxicity of such triazines, the maximum level of application basically is limited only by the esthetics of the mode of administration. As a practical matter, however, such effective amount normally will not be greater than about $10^3$ mcg./12 cm.$^2$, although such amount can be about $10^5$ mcg./12 cm.$^2$ or higher, if desired. Thus, dose levels can range from about 1 mcg./12 cm.$^2$ to about $10^5$ mcg./12 cm.$^2$ skin surface area, preferably from about 1 mcg./12 cm.$^2$ to about $10^3$ mcg./12 cm.$^2$ The effective amount cannot be defined more precisely because of variations in compound potencies, effects of carriers, and other factors discussed below.

The optimum dose level for any given triazine depends upon a number of factors, such as the nature and severity of the inflammatory condition, the potency of the triazine, the concentration of the triazine in the topically applied composition or medicament, the nature of the composition or medicament vehicle, the presence of absorption adjuvants, and the lipid solubility of the triazine. For a discussion of factors involved in the topical absorption of drugs, see "Remington's Pharmaceutical Sciences," 14th Ed., Mack Publishing Company, Easton, Pennsylvania, 1970, pp. 741–746.

The anti-inflammatory triazines can be administered one or more times daily, with multiple applications being preferred. Such multiple applications typically will range from about two to about four per day.

The topical administration of the anti-inflammatory triazines can be made according to any of the well known prior art procedures, which include inunction, spraying, painting, and the like, as well as dispensing from conventional surgical gauze dispensers, collodion, absorbable gelatin film, petrolatum gauze, zinc gelatin, and the like. Thus, such administration can utilize aerosols, creams, emulsions, lotions, oils, ointments, solutions, and the like. In each case, the compounds to be employed in accordance with the present invention are utilized in combination with one or more adjuvants suited to the particular mode of application. For example, ointments and solutions for topical administration can be formulated with any of a number of pharmaceutically acceptable carriers, including ethanol, animal and vegetable oils, mixtures of waxes, solid and liquid hydrocarbons, glycols, and the like.

Such terms as "adjuvants" and "pharmaceutically acceptable carriers" are meant to include cosmetic carriers and bases, such as ethanol and other organic solvents; oil-in-water and water-in-oil emulsions, employed as both creams and lotions; anhydrous systems, comprising, for example, vegetable waxes, vegetable oils, paraffin waxes, paraffin oils, and combinations thereof; and hydrous gels, utilizing, for example, gelatin, xanthate gums, synthetic resins, and the like as gelling agents. Because the triazines disclosed herein require topical application, the use of cosmetic carriers and bases is particularly important, as will be recognized by those skilled in the art.

As already indicated, the present invention also provides a composition suitable for topically treating inflammation in a warm-blooded mammal which comprises a pharmaceutically acceptable carrier and an effective amount of a compound as defined hereinbefore for use in the method of the present invention.

Examples of suitable pharmaceutically acceptable carriers include, among others, the following: organic solvents, such as ethanol, propanol, isopropanol, ethyl acetate, diethyl ether, petroleum ether, and the like; vegetable oils, such as peanut oil, almond oil, sesame oil, olive oil, coconut oil, cocoa butter, and the like; hydrocarbons, such as petrolatum, mineral oil, and the like; hydrocarbon waxes, such as ozokerite, paraffin wax, ceresin, and the like; fatty acids and alcohols and derivatives thereof, such as stearic acid, palmitic acid, stearyl alcohol, cetyl alcohol, lauryl alcohol, isopropyl myristate, butyl stearate, and the like; polyoxyethylene monoalkyl ethers, such as the cetyl, stearyl, and oleyl ethers of ethylene oxide polymers, and the like; non-vegetable waxes, such as lanolin, spermaceti, beeswax, carnauba wax, candelila wax, and the like; polyols, such as glycerin, ethylene glycol, propylene glycol, sorbitol 70, polyethylene glycols, and the like; mono- and di-fatty acid esters of ethylene glycol, diethylene glycol, polyethylene glycols, propylene glycol, glycerol, sorbitol, sorbitan, mannitol, pentaerythritol, polyoxyethylene sorbitol, polyoxyethylene sorbitan, and the like; and miscellaneous materials such as the silicones and the like. The preferred pharmaceutically acceptable carriers are those carriers comprising one or more components at least one of which has a boiling point above about 95° C. and constitutes from about 10 percent to 100 percent (w/w) of such carrier. Thus, the preferred carriers are those listed hereinbefore, except for organic solvents; such organic solvents can be employed, however, provided that the total amount of such solvents in the carrier is less than about 90 percent (w/w) of the total carrier composition.

The term "effective amount" already has been defined. The term "composition" as used herein means the final, topical triazine-containing preparation. As indicated hereinabove, such composition comprises a pharmaceutically acceptable carrier and an amount of anti-inflammatory triazine effective for the topical treatment of inflammation.

The concentration of the anti-inflammatory triazine in the composition or final topical preparation is not critical, provided that the concentration is sufficient to permit the application of at least about 1 mcg. of triazine per 12 cm.$^2$ of skin surface area. In general, the concentration of triazine in the composition will be sufficient to permit the application of the triazine within the effective amount range limits discussed hereinbefore. Such concentration can range from about 0.001 percent to about 50 percent (w/w or w/v), or higher. Preferably, such concentration will be in the range of from about 0.01 percent to about 10 percent.

If desired, the composition or final topical preparation can contain one or more components having pharmaceutical or other activities separate and distinct from the activity of the triazines. Examples of such components include, among others, insect repellants, topical anesthetics, bacteriostats, fungicides, astringents, sunscreen agents, and the like. Alternatively, the triazines can be incorporated into existing or known compositions, such as antiseptics, topical anesthetics, protectives and adsorbents, demulcents, emollients, astringents, antiphlogistics, antipruritics, and the like, the preparation and use of which are well known to those having ordinary skill in the art; see, for example, "Remington's Pharmaceutical Sciences," supra, pp. 763–786. Of particular preference is the incorporation of such triazines into cosmetic formulations, such as sunscreen, suntan, and sunburn preparations.

In accordance with well known procedures, the composition or final topical preparation can contain, in addition to components already described, solvents, preservatives, emulsifiers, surface active agents, perfumes, water, and the like.

By way of example only, some representative triazine-containing compositions follow. Unless otherwise indicated, all percentages are w/w.

| Ointment | Percent |
|---|---|
| Triazine | 10 |
| Polyethylene glycol 400 (N.F.) | 55 |
| Polyethylene glycol 4000 (U.S.P.) | 35 |
| Perfume | q.s. |
| Lotion | |
| Triazine | 1 |
| Ethyl alcohol (denatured) | 69 |
| Oleyl alcohol | 10 |
| Water | 20 |
| Perfume | q.s. |
| Lotion | |
| Triazine | 1 |
| L-43 Silicone" | 5 |
| Ethyl alcohol | 94 |
| Perfume | q.s. |
| "Union Carbide Corp., New York | |
| Oil | |
| Triazine | 2 |
| Castor Oil | 90 |
| Butylated hydroxytoluene | 0.02 |

-continued

| | |
|---|---|
| Ethanol | to 100 |
| Perfume | q.s. |
| Anesthetic ointment | |
| Benzocaine | 5 |
| Triazine | 3 |
| Methylparaben | 0.025 |
| Propylparaben | 0.015 |
| Sodium lauryl sulfate | 1 |
| Propylene glycol | 11 |
| Stearyl alcohol | 24 |
| White petrolatum | 24 |
| Perfume | q.s. |
| Water | to 100 |
| Protective ointment | |
| Zinc oxide | 20 |
| Triazine | 3 |
| Mineral oil | 15 |
| White wax | 3.1 |
| White petrolatum | 58.9 |
| Perfume | q.s. |
| Sunscreen/Insect repellent cream | |
| Triazine | 2 |
| Castor oil | 10 |
| N,N-Diethyltoluamide | 15 |
| Ethyl p-dimethylaminobenzoate | 2 |
| Glyceryl monostearate | 10 |
| Stearic acid | 2 |
| Ethoxylated lanolin alcohol | 2 |
| Butylated hydroxytoluene | 0.02 |
| Cellosize QP 15,000" | 0.25 |
| Methylparaben | 0.15 |
| Triethanolamine | 1 |
| Perfume oil | 0.5 v/w |
| Water | to 100 |
| "Union Carbide Corp., New York | |
| Sunscreen oil | |
| Triazine | 1 |
| Octyl p-dimethylaminobenzoate | 1 |
| Silicone fluid L-45 (100, cS) | 10 |
| Isopropyl palmitate | 88 |
| Aerosol sunscreen oil | |
| Triazine | 1 |
| Ethyl p-dimethylaminobenzoate | 5 |
| Isopropyl myristate | 25 |
| L-43 Silicone" | 5 |
| Perfume oil | 1.25 |
| Lanolin oil | 2.5 |
| Menthol Racemic U.S.P. | 0.25 |
| Absolute alcohol | 60 |
| Fill | |
| Concentrate | 20 |
| Propellant 11/12 (75:25)$^b$ | 80 |
| "Union Carbide Corp., New York | |
| $^b$Trichlorofluoromethane/dichlorodifluoromethane | |
| Palliative preparation for sunburn | |
| Triazine | 5 |
| Colloidal calamine | 10 |
| Triethanolamine stearate | 4.8 |
| Liquid paraffin | 10 |
| Water | 70.2 |
| Antiseptic | q.s. |
| Suntan preparation | |
| Triazine | 1.7 |
| Dihydroxyacetone | 4 |
| Ethanol (95%) | 28 |
| Methyl p-hydroxybenzoate | 1 |
| Sorbitol syrup (70%) | 3 |
| Boric acid powder | 1 |
| Allantoin | 0.3 |
| Distilled water | 59 |
| Perfume | 2 |

The following examples further illustrate the preparations of the compounds employed in the present invention.

EXAMPLE 1

Preparation of
3-Chloro-5,6-bis(4-methoxyphenyl)-1,2,4-triazine

A. 3-Hydroxy-5,6-bis(4-methoxyphenyl)-1,2,4-triazine

Two moles, 540 g., of anisil (4,4'-dimethoxybenzil), 222 g. (2 moles) of semicarbazide hydrochloride, 180 g. (2.2 moles) of sodium acetate, and 2.5 liters of acetic acid were heated at reflux overnight. The cooled reaction mixture was poured into 5 liters of water. The crude solid product was collected by filtration, washed with water, and recrystallized from acetic acid, giving 434 g. of 3-hydroxy-5,6-bis(4-methoxyphenyl)-1,2,4-triazine, m.p. about 272°–274° C.

Analysis: $C_{17}H_{15}N_3O_3$
Calc: C, 66.01; H, 4.89; N, 13.58
Found: C, 65.92; H, 5.04; N, 13.66

B. 3-Chloro-5,6-bis(4-methoxyphenyl)-1,2,4-triazine.

Ten grams of 3-hydroxy-5,6-bis(4-methoxyphenyl)-1,2,4-triazine and 50 ml. of phosphorous oxychloride were heated at reflux for 1.5 hours. The cooled mixture was poured onto crushed ice and the resultant mixture was extracted with diethyl ether. The extract was washed successively with 2 percent sodium hydroxide and water until the washings were neutral. The ether extract was dried over anhydrous sodium sulfate and evaporated. The residue was taken up in diethyl ether, filtered, and the filtrate was evaporated to yield 9.0 g. of 3-chloro-5,6-bis(4-methoxyphenyl)-1,2,4-triazine, m.p. about 130°–132° C.

Analysis: $C_{17}H_{14}ClN_3O_2$
Calc: C, 62.30; H, 4.31; Cl, 10.82; N, 12.82
Found: C, 62.50; H, 4.48; Cl, 10.53; N, 12.99

EXAMPLE 2 preparation of
3-Chloro-5,6-bis(4-fluorophenyl)-1,2,4-triazine

A. 5,6-Bis(4-fluorophenyl)-3-hydroxy-1,2,4-triazine.

A mixture of 23.3 g. of 4,4'-difluorobenzil, 12.1 g. of semicarbazide hydrochloride, 8.8 g. of sodium acetate, and 200 ml. of acetic acid was heated at reflux overnight. The reaction mixture was diluted with 200 ml. of water. The solid which precipitated was isolated by filtration and recrystallized from 90 percent (v/v) ethanol to give 13.6 g. of 5,6-bis(4-fluorophenyl)-3-hydroxy-1,2,4-triazine, m.p. about 263°–266° C.

Analysis: $C_{15}H_9F_2N_3O$
Calc: C, 63.16; H, 3.18; N, 14.73
Found: C, 63.37; H, 3.35; N, 14.52

B. 3-Chloro-5,6-bis(4-fluorophenyl)-1,2,4-triazine.

A mixture of 7.1 g. of 5,6-bis(4-fluorophenyl)-3-hydroxy-1,2,4-triazine and 50 ml. of phosphorous oxychloride was heated at reflux for 2 hours. The reaction solution was poured into water and the resulting mixture was extracted with diethyl ether. The ether extract was washed with water and dried over anhydrous sodium sulfate. The ether was distilled under reduced pressure and the solid residue was recrystallized from ethyl acetate, giving 2.1 g. of 3-chloro-5,6-bis(4-fluorophenyl)-1,2,4-triazine, m.p. about 185°–192° C.

EXAMPLE 3

Preparation of
3-Chloro-5,6-bis(4-chlorophenyl)-1,2,4-triazine

A. 5,6-Bis(4-chlorophenyl)-3-hydroxy-1,2,4-triazine.

A mixture of 55.8 g. of 4,4'-dichlorobenzil, 24.5 g. of semicarbazide hydrochloride, 18.1 g. of sodium acetate, and 400 ml. of acetic acid was heated at reflux overnight. The reaction mixture was diluted with 300 ml. of water. The solid which precipitated was isolated by filtration. The solid was taken up in ethanol and the resulting solution was cooled. The solid which crystallized was isolated by filtration. The filtrate was concentrated to dryness under reduced pressure and the solid residue was recrystallized three times from ethanol to give 4.7 g. of 5,6-bis(4-chlorophenyl)-3-hydroxy-1,2,4-triazine, m.p. about 237°–240° C.

Analysis: $C_{15}H_9Cl_2N_3O$
Calc: C, 56.63; H, 2.85; N, 13.21
Found: C, 56.49; H, 2.80; N, 12.94

B. 3-Chloro-5,6-bis(4-chlorophenyl)-1,2,4-triazine.

A mixture of 1 g. of 5,6-bis(4-chlorophenyl)-3-hydroxy-1,2,4-triazine and 10 ml. of phosphorus oxychloride was heated at reflux until the reaction solution began to darken. The reaction mixture was concentrated to dryness under reduced pressure. The oil which remained was dissolved in diethyl ether. Upon cooling the ether solution, a solid was induced to precipitate, which solid was identified by nuclear magnetic resonance analysis as 3-chloro-5,6-bis(4-chlorophenyl)-1,2,4-triazine, m.p. about 162°–166° C.

What is claimed is:
1. The compound of the formula,

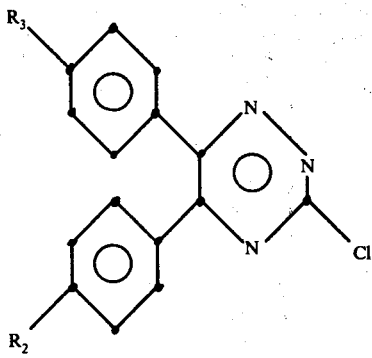

wherein $R_2$ and $R_3$ independently are halo, $C_1$–$C_3$ alkoxy, or di($C_1$–$C_3$ alkyl)amino;
and the pharmaceutically-acceptable acid addition salts of basic members thereof.

2. The compound of claim 1, wherein $R_2$ and $R_3$ are $C_1$–$C_3$ alkoxy and are the same.

3. The compound of claim 2, which compound is 3-chloro-5,6-bis(4-methoxyphenyl)-1,2,4-triazine.

4. The compound of claim 1, which compound is 3-chloro-5,6-bis(4-dimethylaminophenyl)-1,2,4-triazine.

5. The compound of claim 1, which compound is 3-chloro-5,6-bis(4-fluorophenyl)-1,2,4-triazine.

6. The compound of claim 1, which compound is 3-chloro-5,6-bis(4-chlorophenyl)-1,2,4-triazine.

7. A method of treating inflammation in a warm-blooded mammal which comprises topically administering to such mammal an effective amount of a compound of the formula,

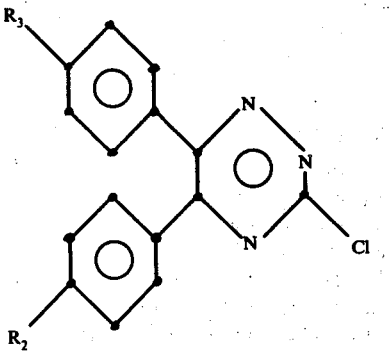

wherein $R_2$ and $R_3$ independently are halo, $C_1$–$C_3$ alkyl, $C_1$–$C_3$ alkoxy, or di($C_1$–$C_3$ alkyl)amino;
and the pharmaceutically acceptable acid addition salts of basic members thereof.

8. The method of claim 7, wherein such inflammation is induced by ultraviolet radiation.

9. The method of claim 8, wherein the compound is 3-chloro-5,6-bis(4-methoxyphenyl)-1,2,4-triazine.

10. The method of claim 8, wherein the compound is 3-chloro-5,6-bis(4-dimethylaminophenyl)-1,2,4-triazine.

11. The method of claim 8, wherein the compound is 3-chloro-5,6-bis(4-fluorophenyl)-1,2,4-triazine.

12. The method of claim 8, wherein the compound is 3-chloro-5,6-bis(4-chlorophenyl)-1,2,4-triazine.

13. The method of claim 8, wherein the compound is 3-chloro-5,6-bis(4-methylphenyl)-1,2,4-triazine.

14. The composition suitable for topically treating inflammation in a warm-blooded mammal which comprises a pharmaceutically acceptable carrier comprising one or more components at least one of which has a boiling point above about 95° C. and constitutes from about 10 percent to 100 percent (w/w) of such carrier, and an effective amount of a compound of the formula,

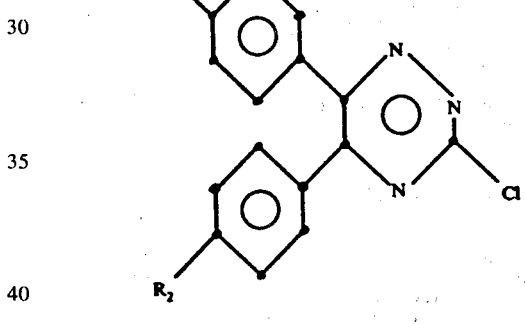

wherein $R_2$ and $R_3$ independently are halo, $C_1$–$C_3$ alkyl, $C_1$–$C_3$ alkoxy, or di($C_1$–$C_3$ alkyl)amino; and the pharmaceutically acceptable acid addition salts of basic members thereof.

15. The composition of claim 14, wherein the compound is 3-chloro-5,6-bis(4-methoxyphenyl)-1,2,4-triazine.

16. The composition of claim 14, wherein the compound is 3-chloro-5,6-bis(4-dimethylaminophenyl)-1,2,4-triazine.

17. The composition of claim 14, wherein the compound is 3-chloro-5,6-bis(4-fluorophenyl)-1,2,4-triazine.

18. The composition of claim 14, wherein the compound is 3-chloro-5,6-bis(4-chlorophenyl)-1,2,4-triazine.

19. The composition of claim 14, wherein the compound is 3-chloro-5,6-bis(4-methylphenyl)-1,2,4-triazine.

* * * * *